United States Patent
Driller et al.

(10) Patent No.: US 6,500,869 B1
(45) Date of Patent: *Dec. 31, 2002

(54) SUN-PROTECTION FORMULATIONS ACTIVE AGAINST HERPES SIMPLEX VIRUSES

(75) Inventors: Hansjürgen Driller, Otzberg (DE); Sabine Hitzel, Messel (DE)

(73) Assignee: Merck Patent Gesellschaft, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/623,982
(22) PCT Filed: Mar. 10, 1999
(86) PCT No.: PCT/EP99/01535
§ 371 (c)(1), (2), (4) Date: Sep. 12, 2000
(87) PCT Pub. No.: WO99/47109
PCT Pub. Date: Sep. 23, 1999

(30) Foreign Application Priority Data

Mar. 18, 1998 (DE) .......................................... 198 11 692

(51) Int. Cl.⁷ ............................................ A61K 39/245
(52) U.S. Cl. ......................... 514/931; 424/401; 424/59
(58) Field of Search .................... 424/401, 59; 514/931

(56) References Cited

U.S. PATENT DOCUMENTS 4,828,825 A * 5/1989 Weber et al. .................. 424/59
5,747,011 A * 5/1998 Ross et al. ..................... 424/59
6,180,662 B1 * 1/2001 Lanzendorfer et al. ..... 514/456

FOREIGN PATENT DOCUMENTS

| DE | 4229713 | 3/1994 |
| DE | 4 229 713 A1 * | 3/1994 |
| EP | 46451 | 2/1982 |
| EP | 898955 | 3/1999 |

OTHER PUBLICATIONS

Van der Molen, Renate Immunoprotection by Sunscreens; Thesis University Leiden. ISBN 90–9013979–6, Leiden 2000.

* cited by examiner

Primary Examiner—Jose' G. Dees
Assistant Examiner—Konata M. George
(74) Attorney, Agent, or Firm—Millen, White, Zelano & Branigan, P.C.

(57) ABSTRACT

The invention relates to sun-protection formulations in solid or liquid form, containing organic and/or inorganic sun-screen filters having a prophylactic action against herpetic diseases of the skin, and to the use of said sun-screen formulations.

6 Claims, No Drawings

SUN-PROTECTION FORMULATIONS ACTIVE AGAINST HERPES SIMPLEX VIRUSES

The present invention relates to sunscreen formulations in solid or liquid form comprising organic and/or inorganic light protection filters having prophylactic action against herpetic diseases of the skin, and to the use of these sunscreen formulations.

As is known, the skin is sensitive to solar rays, which can cause simple sunburn or an erythema, but also burns of varying severity.

However, solar rays also have other negative effects: they cause the skin to lose its elasticity and form wrinkles, thus leading to premature ageing. Dermatoses may also sometimes be observed. In extreme cases, some people can develop skin cancer.

In addition, it is known that for people who have been infected with Herpesviruses and suffer from Herpes under stress, the Herpesviruses are activated in many cases following intensive solar irradiation, leading to herpetic diseases of the skin, in particular in the mouth and lip area.

The most dangerous solar rays are the ultraviolet rays having a wavelength of less than 400 nm. The majority of the undesired effects of sunlight, such as, for example, sunburn, light-induced cell damage and skin cancer, are caused by UVB radiation (280–320 nm).

UVB radiation can cause skin reddening and damage to the cell nuclei by three different reaction paths:

sunburn as a result of the release of biological "messengers", skin cancer as a result of direct damage to the DNA of the cell nucleus, skin cancer as a result of the release of free radicals.

Sunburn is per se exclusively the result of an overdose of UVB radiation. This radiation releases biochemical messengers, such as, for example, histamine, which in turn cause the known effects such as itching, a feeling of pain and heat and "burning" of the skin. The messengers also diffuse into the blood vessels, where they cause dilation, and thus lead to an oedema. In addition, they bring about proliferation of the basal cells.

Solar radiation, including that which does not lead to sunburn, thus signifies stress for the skin cells, as the result of which the defence mechanisms against infection, or the undesired action of bacteria or viruses, are weakened. A latent herpes infection can thus be activated and manifest itself in the formation of painful blisters.

The effects of an overdose of UVB irradiation are observed at the earliest about 4 hours after irradiation, i.e. too late for any preventive measures. Sunburn is therefore not a warning signal, but an indication of skin damage which is already present.

UVA radiation having wavelengths greater than 340 nm is, in the case of healthy skin, principally responsible for the process of skin ageing. In addition, however, a carcinogenic effect is discussed for UVA radiation too.

It is also known that as a result of the presence of the ozone layer in the earth's atmosphere, which absorbs some solar radiation, the lower limit of the ultraviolet rays which reach the surface of the earth is about 280 nm. Chronic cell damage, such as skin ageing and skin cancer, are caused by direct damage of the cell nucleus, which has specific sensitivity to UV radiation having wavelengths below 320 nm. Only at wavelengths above 340 nm does it no longer absorb radiation. Damage to the cell nucleus is based on damage to the DNA. This leads to loss of functionability of the DNA, irrespective of how the damage occurs.

However, the wavelength range of sunlight extends not only beyond the range of UVA and UVB radiation from 280 to 400 nm. The area which can be perceived by the eye extends to 800 nm and is limited by the transition to long-wave infra-red radiation, which is perceived as heat radiation. At the bottom end, the radiation crosses into the short-wave UV region, also called UVC radiation. This is the wavelength range from 100 to 280 nm.

Sunlight in the wavelength range from 400 to 800 nm (VIS region) can penetrate into the deeper layers of skin, where it can become active in a harmful manner, meaning that this very effect of light too can accelerate skin ageing processes. This is also true of IR radiation. Thus, not only UVA and UVB radiation have a harmful effect on the skin cells and cause not only immediately visible short-term damage, such as sunburn and herpes, but also long-term skin changes and skin damage, but also radiation in the wavelength range of visible light (VIS region) and in the region of infra-red radiation (IR region) contributes to skin damage and weakens its defence mechanisms.

It therefore appears desirable to provide sunscreen formulations which ensure as broad a protection as possible against the skin-damaging effect of solar irradiation. In particular, it is, however, also desirable to provide sunscreen formulations which have a prophylactic action against herpetic diseases of the skin.

The invention therefore provides sunscreen formulations comprising organic and/or inorganic light protection filters having prophylactic action against herpetic diseases of the skin, in particular of the skin in the mouth and lip area.

Sunscreen formulations according to the invention have a prophylactic action against herpetic diseases of the skin caused by viruses of the group consisting of herpes simplex and herpes labialis.

The invention therefore provides sunscreen formulations comprising one or more light protection filters or light protection filter combinations which absorb radiation in the UVA and UVB region.

Light protection filters or light protection filter combinations present can advantageously also absorb in the IR region and/or visible region.

The invention further provides for the use of sunscreen formulations which comprise organic and/or inorganic light protection filters for the prophylaxis against herpetic diseases of the skin, in particular against those diseases of the skin in the mouth and lip area which are caused by viruses of the group consisting of herpes simplex and Herpes labialis.

In particular, the use of sunscreen formulations which comprise organic and/or inorganic light protection filters and absorb in the UVA, UVB, IR and visible region of the light spectrum, for the prophylaxis against herpetic diseases of the skin caused by viruses of the group consisting of herpes simplex and Herpes labialis is provided for by the invention.

The sunscreen filters customary today in cosmetics are divided into UVA and UVB filters. For both UVA and UVB regions there are many tried and tested substances known from the specialist literature, substances here by way of example being only those such as phenylbenzimidazole-5-sulfonic acid (Eusolex® 232), benzophenone derivatives (Eusolex® 4360), benzoyl- or dibenzoylmethane derivatives (Eusolexe 9020 or Parsol® 1789, Eusolex 8020), triazone derivatives (octyltriazone, Uvinul T150®), salicylate derivatives (Eusolex HMS®, Eusolex OS®), benzylidin-ecamphor derivatives (Eusolex® 6300), octocrylene (Eusolex® OCR), 4-aminobenzoic acid (PABA) or 2-ethyl N,N-dimethyl-4-aminobenzoate (Eusolex® 6007). Also suitable are light protection filters from the group of methoxycinnamic esters (e.g. Eusolex® 2292) or inorganic light protection filters from the group consisting of titanium dioxide and zinc oxide.

The substances of cinnamic acid derivatives, in particular octyl p-methoxycinnamate, function not only as light protection filters, but also as solvents for other UV filters and are therefore often used in combination with various filters. Since, for example, 2-ethylhexylmethoxycinnamic acid, available commercially under the name Eusolex® 2292, is a very good solvent for other UV filters, it is preferably used in combination with other UV filters, as a result of which an increased overall concentration of light protection filter present is achieved in prepared formulations.

To increase the photostability of light protection filters of the cinnamic acid class, it is also possible to use [lacuna] in the presence of the substance ethyl 3-(N-butylacetamino) propionate, as a result of which an insect-repelling action is achieved at the same time. This substance is a very polar oil which differs from traditional cosmetic oils by virtue of its miscibility with water and oils, and exhibits virtually no toxic or allergic reactions towards the skin.

The combination of ethyl 3-(N-butylacetamino) propionate with Eusolex® 2292 is therefore so highly suitable for introducing UV filters which are otherwise soluble only in low concentrations into the cosmetic preparations, in addition with increased photostability.

Light protection filters which are effective in the wavelength range from 400 to 800 nm (VIS filters) can be soluble or insoluble substances or mixtures of soluble and insoluble substances in cosmetic formulations. These may be pigments and/or dyes which reflect and/or adsorb in the visible wavelength range (VIS-reflecting). Such pigments can, in particular, be golden, red, orange, copper- or body-coloured interference pigments which resemble very closely the natural colour of the skin.

The interference pigments are preferably platelet-shaped or ground mica having a diameter of up to 15 $\mu$m which is coated with $SnO_2$ and/or $TiO_2$. Interference pigments whose carrier material does not consist of mica are, however, also suitable. The coatings may be doped in various ways, such as, for example, by iron or cerium.

In a particular embodiment of such pigments suitable as VIS filters, the mica has a thin coating consisting of up to 1% by weight of $SnO_2$, and a coating consisting of 50–70% by weight, preferably 54–60% by weight, of $TiO_2$ having a rutile structure.

The mica may also have a thin coating consisting of up to 1% by weight of $SnO_2$, and a coating consisting of 50–70% by weight, preferably 54–60% by weight, of $TiO_2$ having an anatase structure, or may have a coating consisting of 50–70% by weight, preferably 54–60% by weight, of $TiO_2$ having an anatase structure.

Suitable substances which can be used in cosmetic formulations and are effective as VIS filters are pearlescent pigments consisting of mica or other carrier materials which are coated with titanium dioxides or iron oxides; in particular, these are silver pigments (mica+$TiO_2$) having particle sizes <200 $\mu$m, in particular <15 $\mu$m, such as, for example, the commercially available Timiron MP 1005® or MP 1001®, and also coarser fractions interference pigments (mica+$TiO_2$) having particle sizes <200 $\mu$m, in particular <5–25 $\mu$m, with golden, red, orange, copper- or body-coloured interference, such as, for example, Timiron Silk Red® or Silk Gold® or Super Red® and Super Gold® or Super Copper® or coarser fractions or other interference colours and mixtures thereof gold pigments (mica with $TiO_2$ and iron oxides) having particle sizes <200 $\mu$m, in particular <5–25 $\mu$m or <15 $\mu$m; such a gold pigment is, for example, Timiron MP 20®, but coarser gold pigment fractions are also suitable coloured pigments (mica with $TiO_2$ and iron oxides) having particle sizes <200 $\mu$m, in particular <5–25 $\mu$m or <15 $\mu$m. Suitable coloured pigments are, for example, Dichrona® or Microna® matt.

Also suitable are VIS-absorbing or -reflecting fillers, such as, for example, mica coated with $TiO_2$ and/or $BaSO_4$. These also include, for example, Biron® (BiOCl), Low Luster® or Extender W®, provided they are not 100% transparent.

Suitable inorganic UV filters are microfine ZnO and $TiO_2$ particles which optionally also reflect or absorb in the VIS region. These are available commercially under the names Hombitec® or Sachtotec®, Kemira M160®, Tioveil AQ® and, to a limited extent, Eusolex T-2000®, limited because it has very high transparency.

These substances have the advantage of not displaying toxic or allergic reactions towards the skin. They have a high light protection factor and therefore a long-lasting protective action. In addition to their protection action in the VIS region, they can also have a protective action in the UV or IR region.

As VIS filters, dyes approved in cosmetics can also be effective, for example those chosen from the "Blaue Liste" (Blue List) (list of dyes approved in cosmetics) ["Blaue Liste" Editio Cantor Verlag, editor H. P. Fiedler (1993)], which can be used individually or as a mixture. These dyes can be used as undissolved pigments. Of particular suitability here are the red, yellow and blue dyes which, individually or in a mixture with the other additives, lead to formulations which, when applied to the skin, have a natural coloration. It is therefore also possible to use dyes from this list which have colours other than those mentioned, such as, for example, orange or gold. Preference is given to using, as red dyes, those with the names D&C Red, preferably those with the numbers No. 10, C.I. 15630, No. 7, C.I. 15850 and No. 21, C.I. 45380, Acid Red, preferably Acid Red 1, C.I. 18050, Allura Red, trans-alpha, beta- or gamma-carotene, and Pigment Red. Yellow dyes in this respect are those with the names Acid Yellow, preferably Acid Yellow 1, C.I. 10316, Tartrazine, C.I. 19140, Rutin, D&C Yellow No. 7, C.I. 45350, Disperse Yellow, Food Yellow, Natural Yellow, Pigment Yellow, Solvent Yellow. Suitable blue dyes are Acid Blue, preferably Acid Blue 9, C.I. 42090, Acid Blue 80, C.I. 61585, D&C Blue No. 6, C.I. 73000, C-Blue 21, Direct Blue 86.

Apart from the dyes listed in the given list, further VIS-absorbing substances are also suitable, such as, for example, flavonoids or natural or artificial melanin.

Further inorganic UV filters which may be used are UV filters generally known to the person skilled in the art, such as, for example, those from the group consisting of titanium dioxide and zinc oxide.

Suitable VIS filters can be incorporated into cosmetic formulations in concentrations of from 0.5 to about 20% by weight. In this way, it is possible to prepare formulations in which up to 100% of the light protection filters used are VIS filters. These are substances which can be dissolved, dispersed or emulsified in a simple manner with water and oils. The formulations according to the invention, which guarantee effective protection in a very wide wavelength range, can thus be used for the preventive treatment of inflammation and allergies of the skin, for preventing certain types of cancer, optionally also for insect repellency and, in particular, for preventing herpetic diseases of the skin. Even the use of sunscreen formulations with intensive protection against UVA and UVB radiation shows here a good action against the activation of herpesviruses, which are generally known as Herpes simplex. For the mouth and lip area, in experiments which have been performed, formulations which also ensure good VIS protection and comprise light protection filters which absorb in the visible region have proven to be excellent. Said light protection filters can be inorganic filters. Suitable examples are light protection filters based on titanium dioxide and zinc oxide, as described above. The titanium dioxide may be micronized titanium dioxide which is available commercially under the name Eusolex T-2000.

Through suitable choice of light protection filters, or the combination of light protection filters and optionally other additives, the effective components of the sunscreen formulations according to the invention are distributed uniformly in the traditional cosmetic carriers and can, particularly in fatty carriers, form a continuous film; in this way they can be applied to the skin in order to form an effective protective film.

The discovery according to the invention cannot be derived from the prior art by simple inference since sunscreen formulations usually have a composition such that they absorb radiation in the UVB and, recently, also in the UVA region, and not, by contrast, in the visible wavelength range from 400 to 800 nm (VIS region) and in the IR region since the latter types of radiation have hitherto been considered harmless for the skin. However, as has been found, even irradiation in this wavelength range of light has a harmful effect. Although the actual mechanism of damage has not been unequivocally explained, it is certain that this radiation can penetrate into the deeper, thus more active, layers of the skin, where it becomes effective in a damaging manner, meaning that this very effect of light can also accelerate skin ageing processes. This means, irrespective of whether the skin is irradiated by light in the UV, visible or IR wavelength region, that damaging effects for the cells of the skin always arise. As a result, regeneration and protective reaction in the cells are required on the one hand. At the same time, the harmful effect weakens defence reactions of the skin towards bacteria and viruses. In cases of previous infection with herpesviruses or for people with a latent herpes infection, this can lead to activation of the herpesviruses and cause herpetic diseases of the skin. In particular, these diseases affect the mouth and lip area and are caused by viruses of the Herpes simplex group, the form active in the mouth and lip area being of the HSV-1 type and being referred to as Herpes labialis.

We have now found that these undesired diseases of the skin can be avoided if a sunscreen which absorbs radiation in a very wide wavelength range and thus leads to as little damage to the skin cells as possible is applied to the skin, particularly prior to intensive solar irradiation.

Depending on the wavelength range in which they absorb, the light protection filters in the sunscreen formulations according to the invention can be present individually or in combination with one or more light protection filters from other classes of substance, which can likewise be present in an amount of from 0.01 to 40% by weight, preferably from 0.5 to 20% by weight, based on the total weight of the cosmetic preparation. A further very particularly preferred embodiment comprises 3 to 10% by weight. As described, the light protection filters can be replaced by up to 100% by the VIS filters, provided they offer effective protection in a very wide wavelength range. In particular, as stated above, it is also possible to use combinations of different light protection filters which can be both inorganic and organic.

As a result of targeted selection of the individual components, the sunscreen formulations according to the invention have high chemical stability, i.e. cannot undergo hydrolysis, cannot be oxidized, have high thermal stability and high resistance to perspiration.

The sunscreen formulations according to the invention for the protection of the human epidermis against the harmful effect of solar irradiation can, depending on the use, be in various forms customarily used for this type. For example, they can, in particular, be in the form of oily, oily-aqueous, aqueous-alcoholic or oily-alcoholic lotions, emulsions, such as a cream or a milk (W/O or O/W), in the form of oily-alcoholic, oily-aqueous or aqueous-alcoholic gels, dispersions or as solid sticks or powders, or can be formulated as spray or aerosol.

The formulations according to the invention can comprise further cosmetic adjuvants which are customarily used in this type of preparation, such as, for example, thickeners, emollients, moisturizers, surfactants, preservatives, antifoams, perfumes, waxes, lanolin, propellants, dyes and/or pigments which colour the composition itself or the skin, and other ingredients customarily used in cosmetics.

The solubilizer used may be an oil, wax or other fatty substance, a low molecular weight monoalcohol or a low polyol or mixtures thereof. Particularly preferred monoalcohols or polyols include ethanol, isopropanol, propylene glycol, glycerol and sorbitol.

A preferred embodiment of the invention is an emulsion which is in the form of a protective cream or milk and, apart from one or more light protection factors, optionally ethyl 3-(N-butylacetamino)propionate, comprises at least one VIS filter, fatty alcohols, fatty acid esters, in particular triglycerides of fatty acids, fatty acids, alkyl polyglycosides, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a low molecular weight alcohol, such as ethanol, or a glycol, such as propylene glycol, and/or a polyol, such as glycerol, and oils, waxes and fatty acid esters, such as triglycerides of fatty acids.

The sunscreen formulation according to the invention can also be in the form of an alcoholic gel which comprises one or more low molecular weight alcohols or polyols, such as ethanol, propylene glycol or glycerol, and a thickener, such as silica. The oily-alcoholic gels further comprise natural or synthetic oil or wax.

In a dispersion, the dispersant used may be an oil, wax or other fatty substance, a low molecular weight monoalcohol or a low molecular weight polyol or mixtures thereof. Particularly preferred monoalcohols or polyols include ethanol, isopropanol, propylene glycol, glycerol and sorbitol.

A particular embodiment of the present invention consists in solid sticks which consist of natural or synthetic waxes and oils, fatty alcohols, fatty acids, fatty acid esters, lanolin and other fatty substances, and, in addition to care additives, comprise, in particular, inorganic and/or organic light protection filters which absorb as broad as possible a wavelength range of sunlight.

If a sunscreen formulation is formulated as an aerosol, the customary propellants, such as alkanes, fluoroalkanes and chlorofluoroalkanes, are normally used.

If the sunscreen formulation according to the invention is formulated as a spray, aqueous/alcoholic solutions are normally used.

Optionally, one or more chemical substances having self-tanning properties can be added to the formulations. The chemical substances having self-tanning properties which may be used are all natural and synthetic substances known to the person skilled in the art which are suitable for the preparation of cosmetic formulations. These can be either vegetable extracts or synthetic self-tanning agents, such as, for example, dihydroxyacetone or α-ketols.

The sunscreen formulations according to the invention can be prepared using techniques which are well known to the person skilled in the art.

It is assumed that a person skilled in the art can utilize the above description in the widest sense even without further explanation. The preferred embodiments are therefore merely to be regarded as a descriptive disclosure which is in no way limiting.

The same also applies to the example below, which should merely contribute to a better understanding of the present invention and is therefore not suitable for limiting the validity of the present invention to this example.

EXAMPLE

| | Sunscreen cream (W/O) Sun protection factor 20 | | | % |
|---|---|---|---|---|
| A. | Eusolex T-2000 (Art. No. 1.05373) | micron. titanium dioxide | (1) | 3.00 |
| | Eusolex OCR (Art. No. 1.05377) | Octocrylene | (1) | 4.00 |
| | Dehymuls E | Dicocoyl Pentaerythritol Citrate and Sorbitol Sesquioleate (and) Cera Alba (and) Aluminium Stearate | (2) | 6.00 |
| | Arlacel 989 | PEG-7 Hydrogenated Castor Oil | (3) | 1.00 |
| | Beeswax (Art. No. 1.11544) | Cera Alba | (1) | 2.00 |
| | Zinc stearate (Art. No. 1.08865) | Zinc Stearate | (1) | 2.00 |
| | Cetiol J 600 | Oleyl Erucate | (2) | 6.00 |
| | Cetiol V | Decyl Oleate | (2) | 6.00 |
| | Cetiol OE | Dicaprylyl Ether | (2) | 5.00 |
| | Dow Corning 200 (100 cs) | Dimethicone | (4) | 1.00 |
| | DL-α-Tocopherol acetate | Tocopheryl Acetate | (1) | 1.00 |
| B | Eusolex 232 (Art. No. 1.05372) | Phenylbenzimidazole Sulfonic Acid | (1) | 2.00 |
| | Tris (hydroxymethyl) aminomethane (Art. No. 1.08386) | Tromethamine | (1) | 0.88 |
| | Glycerol (about 87%) (Art. No. 1.04091) | Glycerol | (1) | 5.00 |
| | Magnesium sulfate heptahydrate (Art. No. 1.05882) | Magnesium Sulfate | (1) | 1.00 |
| | Allantoin (Art. No. 1.01015) | Allantoin | (1) | 0.20 |
| | Preservative | | | q.s. |
| | Water, demineralized | | ad | 100.00 |

Preparation

To neutralize Eusolex 232, the tris(hydroxy-methyl) aminomethane is dissolved in the water of phase B, and Eusolex 232 is added with stirring. Following complete dissolution, the remaining raw materials of phase B are added and the mixture is heated to 80° C. Heat phase A to 75° C. Slowly stir phase B into phase A, and cool the mixture with stirring.

Comments

Viscosity 83,000 mPas (Brookfield rotational viscometer, spectrometry C, 10 rpm) at 25° C.

Samples comprise, as preservative 0.05% of propyl 4-hydroxybenzoate (Art. No. 1.07427)

0.15% of methyl 4-hydroxybenzoate (Art. No. 1.06757)

Sources of Supply (1) Merck KGaA, Darmstadt (2) Henkel KGaA, Dusseldorf (3) ICI, Essen (4) Dow Corning, Dusseldorf

What is claimed is:

1. A method for providing prophylaxis against herpetic diseases of the skin, caused by viruses selected from the group consisting of Herpes simplex and Herpes labialis, comprising administering to a host in need thereof a sunscreen formulation comprising a) organic or b) inorganic light protection filters or a combination of a) and b) light protection filters and wherein the light protection filters absorb in the UVA, UVB, IR and visible region of the light spectrum.

2. A method for providing prophylaxis against herpetic diseases of the skin comprising administering to a host in need thereof a sunscreen formulation comprising light protection filters which absorb in the ultraviolet region and the IR region and the visible region.

3. The method according to claim 2, wherein the light protection filters are organic or inorganic materials or combinations thereof.

4. The method according to claim 2, wherein the herpetic diseases include the mouth and lips.

5. The method according to claim 4, wherein the herpetic diseases are caused by viruses selected from the group consisting of Herpes simplex and Herpes labialis.

6. The method according to claim 2, wherein the sunscreen formulation is in solid or liquid form.

* * * * *